(12) United States Patent
Antonisse et al.

(10) Patent No.: US 6,468,406 B1
(45) Date of Patent: Oct. 22, 2002

(54) ANION-COMPLEXING COMPOUND, METHOD OF PREPARING THE SAME, AN ION-SELECTIVE MEMBRANE AND A SENSOR PROVIDED WITH SUCH A COMPOUND OR MEMBRANE

(75) Inventors: Martijn Marcus Gabriël Antonisse, Zutphen; David Nicolaas Reinhoudt, Hengelo; Bianca Henriëtte Maria Snellink-Ruël, Oldenzaal; Peter Timmerman, Hengelo, all of (NL)

(73) Assignee: Priva Holding B.V., De Lier (NL)

( * ) Notice: Subject to any disclaimer, the term of this patent is extended or adjusted under 35 U.S.C. 154(b) by 0 days.

(21) Appl. No.: 09/647,818
(22) PCT Filed: Apr. 1, 1999
(86) PCT No.: PCT/NL99/00196
§ 371 (c)(1),
(2), (4) Date: Nov. 27, 2000
(87) PCT Pub. No.: WO99/51570
PCT Pub. Date: Oct. 14, 1999

(30) Foreign Application Priority Data

Apr. 2, 1998 (NL) .............................................. 1008789

(51) Int. Cl.[7] ................... G01N 27/333; C07D 225/04; C07C 335/04
(52) U.S. Cl. ...................... 204/418; 204/416; 540/450; 540/451; 540/460; 564/26; 564/48
(58) Field of Search ................. 204/416, 418; 540/450, 451, 460; 564/26, 48

(56) References Cited

U.S. PATENT DOCUMENTS 5,180,481 A  1/1993  Carey

OTHER PUBLICATIONS

Buehlmann et al (Tetrahedron, vol. 53, pp. 1647–1654, 1997).*
Article: S. Nishizawa, et al.: "Application of a bis–thiourea ionophore for an anion selective electrode with a remarkable sulphate selectivity" Analytica Chimica Acta, vol. 358, 1998 pp. 35–44, XPOO2087233, Amsterdam, NL (cited in the application).
Database WPI Section Ch, Week 9222, Derwent Publ. Ltd., London, GB; AN 92–180877 XP002087234 & JP 04 120049 A (Shingijutsu Jigyodan) Apr. 21, 1992.

* cited by examiner

Primary Examiner—Terrence R. Till
Assistant Examiner—Kaj K. Olsen
(74) Attorney, Agent, or Firm—Darby & Darby

(57) ABSTRACT

The invention is directed to an anion-complexing compound with the formula I wherein R1 is a six-membered ring, Y' is —NHC(X)NH—, and Y" is selected from the group consisting of —NHC(X')—, —C(X')NH—, and —NHC(X') NH—; and wherein X and X', independently of one another, is a sulphur or oxygen atom. R4 and R4' are either identical represented by a variety of groups or together represent a group such that the compound has a macrocyclic structure. The invention is also directed to a method of preparing such a compound, an ion-selective membrane, as well as a sensor provided with such a compound or membrane.

8 Claims, 2 Drawing Sheets

2a

2b

2c

Figure 1:
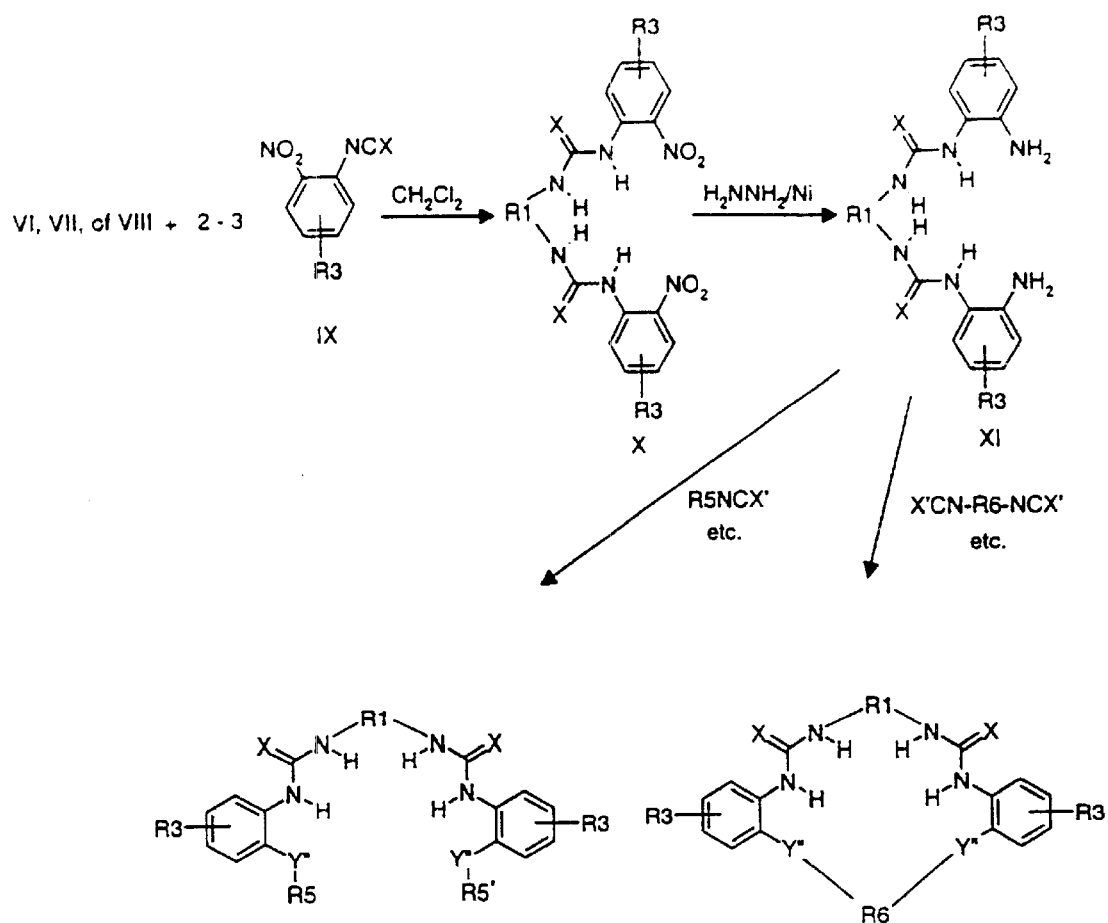

ANION-COMPLEXING COMPOUND, METHOD OF PREPARING THE SAME, AN ION-SELECTIVE MEMBRANE AND A SENSOR PROVIDED WITH SUCH A COMPOUND OR MEMBRANE

FIELD OF THE INVENTION

The present invention relates to an anion-complexing compound with the formula I of the formula sheet, wherein R1 is a rest selected from the group of rests with the formulas II, III, and IV of the formula sheet; of which the ring may or may not be substituted with 1 to 3 R2 groups which may or may not be different from each other, wherein R2 represents alkyl or alkoxy;

Y' represents a —NHC(X)NH-group, and

Y" represents a rest selected from the group —NHC(X')—, —C(X')NH— and —NHC(X')NH—, wherein X and X', independently of one another, represent a sulphur or oxygen atom;

A represents an aromatic 6-ring which may or may not be substituted with 1 or 2 R3 groups, which R3 groups, independently of each other, represent alkyl, alkoxy, $NO_2$, or a halide selected from the group consisting of fluorine and chlorine; and R4, R4' are either
   a) identical, representing aryl that may or may not be substituted with 1 or 2 R3 groups, an alkyl, an acyl and an aryl sulphonyl which may or may not be substituted with 1 or 2 R3 groups;
   or
   b) together form a single rest, which rest is selected from the group of a rest with the formula V of the formula sheet, which may or may not be substituted with 1 or 2 R3 groups, and an alkyl group with the formula —$(CH_2)_n$— wherein n is 2 to 6.

Alkyl in the present application is to be understood to be a hydrocarbon rest which may or may not be branched, having a chain length of 1 to 15 carbon atoms. The term alkoxy is understood to mean an —OR group, wherein R is an alkyl as previously defined. Aryl is understood to be a group according to formula V of the formula sheet, wherein R is as previously defined. An acyl group is understood to be —C(O)R or an —C(O)Ar, wherein R stands for alkyl and Ar for aryl, both as previously defined.

BACKGROUND OF THE PRIOR ART

Nishizawa, S. et al. (ref. 1) describe anion recognition by neutral urea and thiourea compounds with an anion-complexing activity. These compounds differ from the compounds according to the present invention in particular, through the smaller number of hydrogen bonds provided by the (thio)urea groups (2). As R1, which links the (thio)urea group, a rest derived from 1,3-bis(amino methyl) benzene is described.

Buehlmann P. et al. (ref. 2; same authors as ref. 1) have described neutral bis-(thio)urea compounds. The compounds differ from the compounds of the present invention in particular in the smaller number of hydrogen bonds provided by the (thio)urea groups (2). Also described as R1, which binds the (thio)urea groups, is a 2,7-di-tert.-butyl-9,9-dimethyl-4,5-xanthene diamine-derived rest.

Nishizawa, S. et al. (ref. 3) describe the application of compounds disclosed in Ref. 1 for an anion-selective electrode.

Xiao, K. P. et al. (ref. 4, co-authors are among others Nishizawa and Buehlmann) describe the use of the bis-thioureaxanthene derivative described in ref. 2 in a membrane for a chloride-ion-selective electrode.

All the above-described prior art compounds relate to bis(thio)urea compounds capable of donating four hydrogen bonds for binding negatively charged ions. The compounds according to the present invention differ from the known compounds in particular in the larger number (6 or more) of hydrogen bonds provided. Despite the fact that negatively charged ions are still bound by maximally four hydrogen bonds from (thio)urea, the compounds according to the present invention have surprisingly been shown to possess a strong affinity for (dihydrogen) phosphate ions.

SUMMARY OF THE INVENTION

According to a favourable embodiment, Y" represents a (thio)urea group, and R4 and R4' an aryl group.

Surprisingly, a compound according to the present invention in which R4 and R4' are aryl sulphonyl, but in particular aryl, has been found to bind two (dihydrogen) phosphate groups, with the phosphate groups interacting together by means of a hydrogen bond. Without the intention of being bound to any theory, it is believed that said interaction leads to an increased affinity constant that was observed.

According to a further favourable embodiment at least one of X and X' is a sulphur atom.

Such compounds were shown to exhibit higher affinity constants for (dihydrogen)phosphate ions.

According to a further favourable embodiment R1 is substituted with two R2 groups.

It has been found that such compounds are better able to bind anions. Without wishing to be tied to any theory, it is believed that the substituents help to prevent mutual interactions between molecules of the compounds according to the invention, such as hydrogen bonds and π—π stacks, resulting in hydrogen bonds being no longer available for binding anions. Suitable R2 groups are, for example, isopropyl groups.

A method of preparing an anion-complexing compound with formula I of the formula sheet, wherein a compound selected from the group comprising the compounds VI, VII and VIII of the formula sheet and R2 is as previously defined, is reacted with, in respect of the number of $NH_2$ groups, a stoichiometric amount of a compound with the formula IX of the formula sheet, wherein R3 is as previously defined, yielding an intermediate product with the formula X of the formula sheet, with R1 representing the corresponding rest having one of the formulas II, III and IV;

the compound with the formula X is reduced yielding a compound with the formula XI of the formula sheet; and the compound with the formula XI is reacted with a compound selected from the group comprising R5NCX', R5COCl, R5SO$_2$Cl, R6(NCX')$_2$, R6(COCl)$_2$, and R6(SO$_2$Cl)$_2$, wherein R5 represents an aryl which may or may not be substituted with 1 or 2 R3 groups, an alkyl, an acyl and an arylsulphonyl which may or may not be substituted with 1 or 2 R3 groups; and R6 represents a rest selected from the group of a rest with the formula V of the formula sheet, which may or may not be substituted with 1 or 2 R3 groups, and an alkyl group with the formula —$(CH_2)_n$— in which n is 2 to 6, yielding a compound with the formula I.

With respect to the last step it is observed that the reaction with an R5-comprising compound results in non-macro cyclic compounds, and those with an R6-comprising compound result in macro cyclic compounds with the formula I.

DETAILED DESCRIPTION OF THE INVENTION

The invention further relates to an ion-selective membrane comprising a compound according to the invention which is incorporated in a polymeric carrier material.

Such a membrane may be utilized for carrying out separations, analyses, and in particular for sensors. A suitable polymeric carrier material is, for instance, PVC. The compound according to the invention may in accordance with coupling techniques that are known in the art, be coupled to the polymeric carrier material. Alternatively, the compound may also be dissolved in the polymeric carrier material. In particular the groups R2 and R3 could be suitably chosen for this purpose and may, for example, be alkyl.

Therefore the invention also relates to a sensor provided with a compound or a membrane according to the invention.

The sensor itself may be any suitable sensor known in the art, such as an ISFET. The compound may be applied, optionally covalently, to the surface of the sensor, using techniques for coupling molecules to a surface which are generally known in the art.

To the person skilled in the art it will be obvious that the compounds defined in the present application may optionally be substituted with one or more groups that essentially do not change the anion-complexing activity, in other words the affinity and/or the selectivity, of the compounds. This may, for example, be the case if the compound has to be coupled to a carrier or has to be made compatible with a matrix in which it is to be incorporated. Such compounds fall within the scope of the invention.

Figure 2:
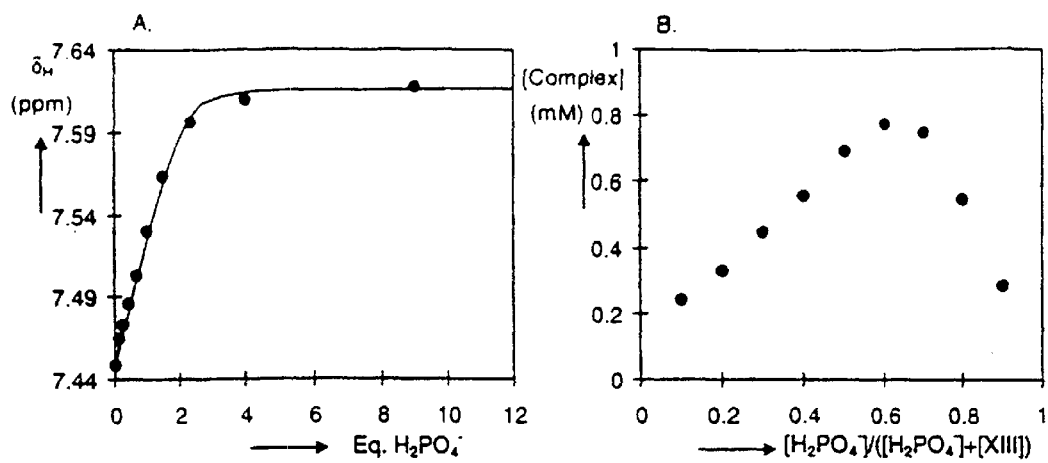
Figure 2:
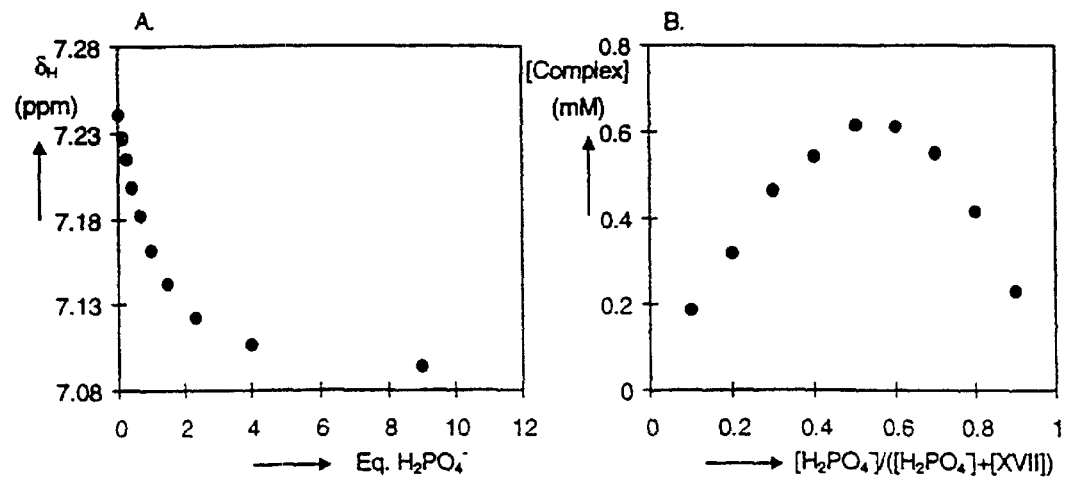
Figure 2:
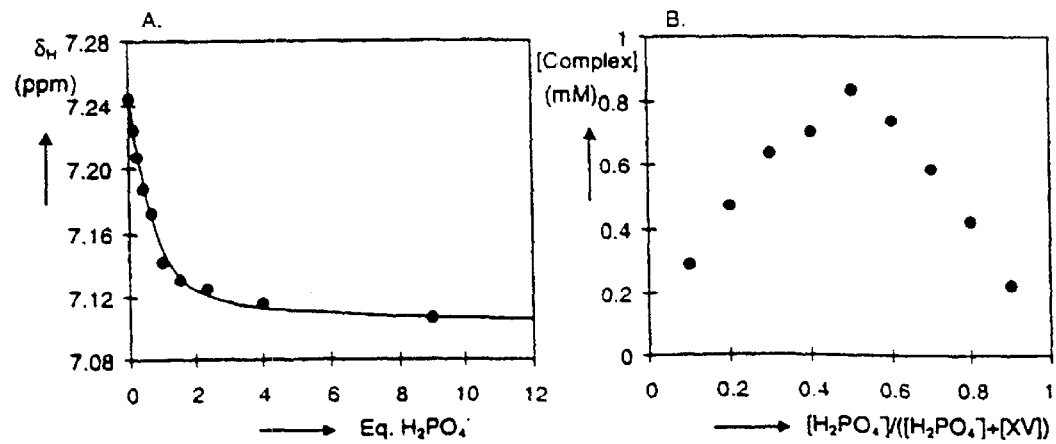

The present invention will now be explained with reference to the exemplary embodiments and the illustration below, in which FIG. 1 represents a reaction scheme for the preparation of compounds according to the invention; and FIGS. 2a, 2b and 2c each show two graphs for a total of three compounds according to the invention. In the left-hand graph the NMR-measured chemical displacement is plotted against the concentration of dihydrogen phosphate. The right-hand graph is a Job-plot of the left-hand graph.

For the preparation of the compounds below, which preparation is schematically illustrated in FIG. 1, and R1, R3, R4, R5, R6, X, X' and Y' have the above definitions, the dimethyl formamide (DMF) used has been distilled in the presence of $CaCl_2$ and stored over molecular sieves (4 Å). Reactions with (thio)isocyanates were performed under argon.

EXAMPLE 1

Tetrakisurea Compound XIII a) 1,3-bis(Methylene(N'-2-nitrophenylureylene))-4,6-diisopropyl-m-xylene 2.3 mmol 1,3-bis(aminomethyl)-4,6-diisopropyl-benzene obtained by the method described in ref. 5) is stirred with 2.6 mmol 2-nitrophenyl isocyanate under a dry argon atmosphere for 4 hours in 200 ml dry $CH_2Cl_2$. The precipitated yellow solid was obtained by filtration and dried under vacuum, yielding the title product.

Yield 1.0 g (80%). Fusion point 258° C. Chemical analysis for $C_{28}H_{32}N_6O_6$; Calculated C: 61.3 H: 5.9 N: 15.3; Found C: 61.2 H: 5.9 N: 15.1.

b) 1,3-bis(Methylene(N'-aminophenylureylene))-4,6-diisopropyl-m-xylene

The bisnitro derivative was dissolved in a 1:1 mixture of tetrahydrofuran and methanol (100 ml). 0.44 ml hydrazine monohydrate was added as well as a catalytic amount (2.5 g; 50% slurry in water) of Raney nickel, and the solution was refluxed overnight. The solution was filtered over Hyflo (Fluka, Buchs, Switzerland) and the solvent evaporated, yielding the title product.

Yield 100%. The product decomposed at 290° C. Chemical analysis for $C_{28}H_{36}N_6O_2$. Calculated C: 68.8 H: 7.4 N: 17.2; Found C: 69.0 H: 7.5 N: 17.4.

Tetrakisurea Compound XIII c) to 0.10 g (0.2 mmol) of the diamine obtained in the previous step in 10 ml dry dimethylformamide 0.5 mmol phenylisocyanate is added. The solution is stirred during the night at room temperature. Water is added to eliminate the excess isocyanate and the solution is concentrated by evaporation. The crude product is stirred with methanol. Filtration yielded the title product as white solid.

Yield 0.11 g (75%). De substance decomposed at 247° C. Chemical analysis for $C_{42}H_{46}N_8O_4$.0.5 MeOH; Calculated C: 68.7 H: 6.5 N: 15.1; Found C: 68.9 H: 6.5 N: 15.1.

EXAMPLE 2

Tetrakisurea Compound XVII

The method of Example 1 is repeated, except that in step c) propyl isocyanate is used instead of phenyl isocyanate.

Yield 0.08 g (60%). The substance decomposed at 245° C. Chemical analysis for $C_{36}H_{50}N_8O_4$.MeOH; Calculated C: 64.3 H: 7.9 N: 16.2; Found C: 64.6 H: 1.5 N: 16.5.

EXAMPLE 3

Tetrakisthiourea Compound XIV

The steps 2 a) and 2 b) are identical with the steps a) and b) of Example 1.

c) Bisurea-bisthiourea Compound XIV

This step was identical with step c) of Example 1, while replacing phenylisocyanate with phenylisothiocyanate.

Yield 0.09 g (60%). Fusion point: 163–166° C. Chemical analysis for $C_{42}H_{46}N_8O_2S_2$.MeOH; Calculated C: 65.3 H: 6.4 N: 14.2 S: 8.1; Found C: 65.1 H: 6.1 N: 14.3 S: 8.3.

EXAMPLE 4

Macro cyclic tetrakisurea compound with the formula XV of the formula sheet.

Starting with 0.25 g (0.51 mmol) of the product obtained in Example 1 step b), the title compound is obtained by dissolving the starting product in 50 ml dry DMF and adding 0.51 mmol 1,3-bis(isocyanatomethyl)benzene. The solution is stirred overnight, the solvent is evaporated and the crude product is stirred with methanol. After filtering the title product is obtained as a white solid.

Yield 0.29 g (85%). The product decomposed at 230° C. Chemical analysis for $C_{38}H_{44}N_8O_4$; Calculated C: 67.4 H: 6.6 N: 16.6; Found C: 67.7 H: 6.6 N: 16.5.

EXAMPLE 5

Macro cyclic tetrakisurea compound with the formula XVI of the formula sheet.

The method described in Example 4 was repeated while replacing 1,3-bis(isocyanatomethyl)benzene with 1,4-diisocyanatobutane. 0.30 g product was obtained (yield 85%) which decomposed at 280° C.

Chemical analysis for $C_{34}H_{44}N_8O_4$; Calculated C: 65.0 H: 7.1 N: 17.8; Found C: 65.2 H: 7.2 N: 18.1.

Studies of Anion-complexing Properties

The ability to bind anions was studied with the aid of 250 MHz $^1$H-NMR spectroscopy in dimethylsulphoxide. To this end 12.5 mmol of a compound according to one of the Examples 1, 2 and 4 were dissolved in 5 ml DMSO-d6. A solution of tetrabutyl ammonium salts of $Cl^-$, $Br^-$, $NO_3^-$, $HSO_4^-$ and $H_2PO_4^-$ (2.5 mmol per liter) in DMSO-d6 was added. The observed displacement of a proton of R1 was plotted against the concentration dihydrogen phosphate (left-hand graphs in FIG. 2). Also, a Job-plot was made based on the measurements.

The Job-plot of the $H_2PO_4^-$-complexing of tetrakisurea compound XIII shows that a maximum complex concentration occurs at a value indicating a ratio of bound $H_2PO_4^-$: XIII of 1.9. Assuming a 2:1 stoichiometry for the complex, an association constant of $5\times10^7$ $M^{-2}$ is calculated. Such an association constant is the upper limit that can be measured with the aid of the used NMR technique. Neither $Br^-$ nor $NO_3^-$ or $HSO_4^-$ induce a displacement in the NMR spectrum. One equivalent $Cl^-$ only results in a small displacement (approximately 0.02 ppm) of the urea protons. The displacements induced by $H_2PO_4$ are much greater. Tetrakisthiourea compound XIV gives an association constant comparable with XIII, the upper limit of the method of detection used (not shown). $Cl^-$ was shown to bind to XIV at a ratio of 1:1 and the association constant was determined at 250 $M^{-1}$.

FIG. 2b shows that the compound according to Example 2 (XVII, in which R4 is an alkyl group), binds dihydrogen phosphate as a 1:1 complex but also as a 1:2 complex (the Job-plot shows a maximum at 0.56). Due to this it is not possible to accurately calculate an association constant.

FIG. 2c shows that the macro cyclic tetrakisurea compound XV of Example 4 binds $H_2PO_4^-$ exclusively in a 1:1 stoichiometry. Based on the displacement measured, an association constant of $2.5\times10^3$ $M^{-1}$ was measured. This compound's complexing of $Cl^-$ results in a displacement of 0.08 ppm at total complexing for the aromatic urea protons at 7.93 and 7.89 ppm. For $Cl^-$ an association constant of 500 $M^{-1}$ was calculated.

The macro cyclic tetrakisurea compound XVI of Example 5 is shown to have a comparable binding strength for $H_2PO_4^-$ ($4.0\times10^3$ $M^{-1}$), but the binding of $Cl^-$ is considerably lower ($K_a<50$ $M^{-1}$) (not shown). Consequently, the compound according to Example binds 5 $H_2PO_4^-$ at least 100 times more selective than $Cl^-$.

REFERENCES

1. Nishizawa, S. et al. Tetrahedron Letters, 36(36), pp. 6483–6486 (1995).
2. Buehlmann, P. et al. Tetrahedron, 53(5), pp. 1647–1654 (1997).
3. Nishizawa, S. et al. Analytica Chimica Acta, 358, pp. 35–44 (1998).
4. Xiao, P. K. et al. Anal. Chem. 69, pp. 1038–1044 (1997).
5. Seto, C. T. et al. J. Am. Chem. Soc. 115, pp. 1321–1329 (1993).

What is claimed is:

1. An anion-complexing compound with the formula I wherein R1 is selected from the group consisting of formulas II and III
    wherein any one of the rings of formulas II and III may be substituted with 1 to 3 R2 groups, wherein R2 is alkyl or alkoxy and may be the same or different from each other;
   wherein Y' is —NHC(X)NH—;
   wherein Y" is selected from the group consisting of —NHC(X')—, —C(X')NH—, and —NHC(X')NH—;
    wherein X and X', independently of one another, is a sulphur or oxygen atom;
   wherein any one of the rings of formula I may be substituted with 1 or 2 R3 groups, wherein R3 is, independently of each other, alkyl, alkoxy, $NO_2$, or a halide, wherein halide is selected from the group consisting of flourine and chlorine; and
   wherein R4 and R4' are either
      a) identical, representing aryl that may be unsubstituted or may be substituted with 1 or 2 R3 groups, an alkyl, an acyl or an aryl sulphonyl, which may be unsubstituted or may be substituted with 1 or 2 R3 groups; or
      b) together form formula V
         wherein the ring of formula V may be substituted with 1 or 2 R3 groups, or an alkyl group with the formula —$(CH_2)_n$—, wherein n is 2 to 6.

2. A compound according to claim 1, wherein Y" is a (thio)urea group, R4 is an aryl group, and R4' is an aryl group.

3. A compound according to claim 1, wherein at least one of X and X' is a sulphur atom.

4. A compound according to claim 1, wherein any one of the rings of formulas II and III are substituted with two R2 groups.

5. An ion-selective membrane comprising a compound according to claim 1, which is incorporated in a polymeric carrier material.

6. A sensor provided with an ion-selective membrane according to claim 5.

7. A sensor provided with a compound according to claim 1.

8. A method of preparing an anion-complexing compound of formula I
   wherein R1 is selected from the group consisting of formulas II and III
      wherein any one of the rings of formulas II and III may be substituted with 1 to 3 R2 groups, wherein R2 is alkyl or alkoxy and may be the same or different from each other;
   wherein Y' is —NHC(X)NH—;
   wherein Y" is selected from the group consisting of —NHC(X')—, —C(X')NH—, and —NHC(X')NH—;
   wherein X and X', independently of one another, is a sulphur or oxygen atom;
      wherein any one of the rings of formula I may be substituted with 1 or 2 R3 groups, wherein R3 is, independently of each other, alkyl, alkoxy, $NO_2$, or a halide, wherein halide is selected from the group consisting of flourine and chlorine; and
   wherein R4 and R4' are either
      a) identical, representing aryl that may be unsubstituted or may be substituted with 1 or 2 R3 groups, an alkyl, an acyl or an aryl sulphonyl, which maybe unsubstituted or may be substituted with 1 or 2 R3 groups; or
      b) together form formula V
         wherein the ring of formula V may be substituted with 1 or 2 R3 groups; or an alkyl group with the formula —$(CH_2)_n$—, wherein n is 2 to 6, which comprises the steps of
- A) reacting a compound selected from the group consisting of the compounds VI and VII wherein any one of the rings of formulas VI and VII may be substituted with 1 to 3 R2 groups, wherein R2 is alkyl or alkoxy, with a stoichiometric amount, with respect of the number of $NH_2$ groups, of a compound with the formula IX wherein the ring of formula IX may be substituted with 1 or 2 R3 groups, wherein R3 is alkyl, alkoxy, $NO_2$, or a halide, wherein halide is selected from the group consisting of flourine and chlorine, yielding an intermediate product with the formula X wherein any one of the rings of formula X may be substituted with 1 or 2 R3 groups;
- B) reducing the compound of the formula X to yield a compound with the formula XI wherein any one of the rings of formula XI may be substituted with 1 or 2 R3 groups;
- C) reacting the compound with the formula XI with a compound selected from the group consisting of R5NCX', R5COCl, R5SO$_2$Cl, R6(COCl)$_2$, R6(COCl)$_2$, and R6(SO$_2$Cl)$_2$, wherein R5 represents an aryl, which may be unsubstituted or may be substituted with 1 or 2 R3 groups, an alkyl, an acyl and an arylsulphonyl, which may be unsubstituted or may be substituted with 1 or 2 R3 groups; and R6 is formula V wherein the ring of formula V maybe substituted with 1 or 2 R3 groups; or an alkyl group with the formula —$(CH_2)_n$— in which n is 2 to 6, yielding a compound with the formula I.

* * * * *